(12) United States Patent
Sadile (10) Patent No.: US 12,383,406 B2
(45) Date of Patent: Aug. 12, 2025

(54) BICOMPARTMENTAL KNEE PROSTHESIS

(71) Applicant: Francesco Sadile, Naples (IT)

(72) Inventor: Francesco Sadile, Naples (IT)

( * ) Notice: Subject to any disclaimer, the term of this patent is extended or adjusted under 35 U.S.C. 154(b) by 726 days.

(21) Appl. No.: 17/630,073

(22) PCT Filed: Apr. 22, 2020

(86) PCT No.: PCT/IB2020/053799
§ 371 (c)(1),
(2) Date: Jan. 25, 2022

(87) PCT Pub. No.: WO2021/019313
PCT Pub. Date: Feb. 4, 2021

(65) Prior Publication Data
US 2022/0265432 A1    Aug. 25, 2022

(30) Foreign Application Priority Data
Aug. 1, 2019   (IT) .......................... 102019000013614

(51) Int. Cl.
*A61F 2/38*  (2006.01)
(52) U.S. Cl.
CPC .................................. *A61F 2/3859* (2013.01)
(58) Field of Classification Search
CPC ........ A61F 2/3859; A61F 2/38; A61F 2/3877; A61F 2/389; A61F 2002/30604; A61F 2002/3895; A61F 2310/00011; A61F 2/30734; A61F 2/30756; A61F 2/30767; A61F 2/30942; A61F 2/30965; A61F 2/3868; A61F 2/3872; A61F 2/4657;
(Continued)

(56) References Cited

U.S. PATENT DOCUMENTS 5,681,354 A * 10/1997 Eckhoff ................ A61F 2/3859
                                                   623/20.35
6,770,099 B2 * 8/2004 Andriacchi ........... A61F 2/3859
                                                   623/20.14
(Continued)

FOREIGN PATENT DOCUMENTS

WO    WO-2020185423 A1 *  9/2020   ........... A61F 2/3859

OTHER PUBLICATIONS

Gender and Side-to-Side Differences of Femoral Condyles Morphology: Osteometric Data from 360 Caucasian Dried Femori (Year: 2012).*

(Continued)

*Primary Examiner* — Melanie R Tyson
*Assistant Examiner* — Paris Marie Blass
(74) *Attorney, Agent, or Firm* — Stetina Garred Brucker & Newboles (57) ABSTRACT

A bicompartmental knee prosthesis or bicondylar prosthesis adapted to be fixed to a femur, the prosthesis comprising
a first portion adapted to define at least part of a medial femoral condyle;
a second portion adapted to define at least part of a lateral femoral condyle;
an interconnecting portion which integrally connects the first portion and the second portion to each other;
the prosthesis being shaped so as to be adapted to leave the native trochlea at least partially uncovered;
characterized in that, along the same axis, a length of the first portion is greater than a length of the second portion.

13 Claims, 6 Drawing Sheets

(58) Field of Classification Search
CPC .. A61F 2002/30011; A61F 2002/30062; A61F 2002/30092; A61F 2002/30116; A61F 2002/30179; A61F 2002/30245; A61F 2002/30387; A61F 2002/30433; A61F 2002/30616; A61F 2002/30624; A61F 2002/30883; A61F 2002/30892; A61F 2002/30894; A61F 2002/30929; A61F 2002/30934; A61F 2002/30948; A61F 2002/30975; A61F 2002/4635; A61F 2210/0004; A61F 2210/0014; A61F 2220/0016; A61F 2220/0025; A61F 2220/0041; A61F 2230/0006; A61F 2230/0028; A61F 2230/0071; A61F 2250/0023; A61F 2310/00017; A61F 2310/00023; A61F 2310/00029; A61F 2310/00047; A61F 2310/00065; A61F 2310/00071; A61F 2310/00077; A61F 2310/00083; A61F 2310/00107; A61F 2310/00113; A61F 2310/00119; A61F 2310/00131; A61F 2310/00149; A61F 2310/00155; A61F 2310/00179; A61F 2310/00329; A61F 2310/00353; A61F 2310/00395; A61F 2310/00592; A61B 17/155; A61B 17/157; A61B 17/1675; A61B 17/1764; A61B 17/14; A61B 17/149; A61B 17/1778; A61B 2017/00734; A61B 2017/1602; A61B 2034/2065; A61B 2090/034; A61B 34/20; A61B 34/30

See application file for complete search history.

(56) References Cited

U.S. PATENT DOCUMENTS

| | | | |
|---|---|---|---|
| 8,114,164 B2* | 2/2012 | Termanini | A61F 2/38 623/20.14 |
| 2006/0058884 A1 | 3/2006 | Aram et al. | |
| 2007/0100462 A1* | 5/2007 | Lang | A61F 2/30942 623/20.29 |
| 2008/0119939 A1 | 5/2008 | Termanini | |
| 2010/0292804 A1 | 11/2010 | Samuelson | |
| 2017/0290669 A1* | 10/2017 | Termanini | A61F 2/38 |

OTHER PUBLICATIONS

Patent Cooperation Treaty, International Search Report for International Application No. PCT/IB2020/053799, mailed Jul. 7, 2020, 10 pages.

* cited by examiner

BICOMPARTMENTAL KNEE PROSTHESIS

CROSS-REFERENCE TO RELATED APPLICATIONS

This application claims priority to PCT International Application No. PCT/IB2020/053799 filed on Apr. 22, 2020, which application claims priority to Italian Patent Application No. 102019000013614 filed on Aug. 1, 2019, the disclosures of which are expressly incorporated herein by reference.

STATEMENT RE: FEDERALLY SPONSORED RESEARCH/DEVELOPMENT

Not applicable.

BACKGROUND OF THE INVENTION

Field of the Invention

The present invention relates to a knee prosthesis. In particular, the invention relates to a bicompartmental knee prosthesis, or more precisely, to a bicondylar prosthesis. The prosthesis is adapted to be fixed to a femur, more particularly is adapted to replace the femoral part of the medial, i.e. internal compartment, and the femoral part of the lateral, i.e. external, compartment of the knee.

Background Art

The knee is a joint formed by the distal end of the femur (distal epiphysis), the proximal end of the tibia (proximal epiphysis), and the kneecap or patella.

The knee consists of three compartments: (i) the medial or internal femoral-tibial compartment; (ii) the lateral or external femoral-tibial compartment; (iii) and the patellofemoral compartment, which is the area between the femur and the patella.

In particular, the distal end of the femur has two convex surfaces, on the frontal and on the sagittal plane, referred to as femoral condyles. One convex surface is referred to as the medial, or internal, femoral condyle, and the other convex surface is referred to as the lateral, or external, femoral condyle.

There is a notch, referred to as the intercondylar fossa, between the two femoral condyles.

The anterior surface of the distal end of the femur is referred to as the trochlea; it faces the patella and is part of the patellofemoral compartment. The trochlea extends, in particular, above the intercondylar fossa.

There are also ligaments which, in particular, give stability to the joint.

The knee prostheses currently available reflect the well-established beliefs of orthopedic surgeons.

In particular, unicompartmental prostheses and tricompartmental prostheses are used today.

A unicompartmental prosthesis is adapted to replace only one of the three knee compartments. For example, a medial unicompartmental prosthesis is adapted to replace only the medial compartment and a lateral unicompartmental prosthesis is adapted to replace only the lateral compartment.

A tricompartmental prosthesis is adapted to replace all three knee compartments. In particular, a tricompartmental prosthesis comprises two portions which define a respective femoral condyle and an additional portion which defines the trochlea. In other words, a tricompartmental prosthesis also comprises a portion which is adapted to cover or replace the trochlea, in particular beyond the portions of both distal and posterior condyles.

It is worth noting that in all tricompartmental prostheses, the height of the medial condyle is less than the height of the lateral condyle.

In some pathological conditions in which both femoral condyles need to be replaced, the choice of surgeons is limited exclusively to the use of a tricompartmental prosthesis or two unicompartmental prostheses, the latter being completely distinct and separate from each other. With two unicompartmental prostheses a so-called "bi-mono" prosthetic implant is obtained.

However, both solutions have several drawbacks.

Very frequently, the choice of surgeons falls on the implant of a tricompartmental prosthesis, even in cases in which the trochlea is, substantially, healthy. Therefore, in these cases, the implant of a tricompartmental prosthesis disadvantageously implies the resection of the healthy trochlea.

On the other hand, the implant of two unicompartmental prostheses is very complex, leading surgeons to opt for a tricompartmental one.

Furthermore, the implant of two unicompartmental prostheses creates harmful imbalances in the overall balance of the forces to which the knee joint is subjected.

Both the implant of a tricompartmental prosthesis and of two unicompartmental prostheses are inadequate, particularly in some cases of gonarthrosis, more particularly in cases of primitive (idiopathic) gonarthrosis when the patellofemoral compartment is not subject to the pathology in progress.

However, as mentioned, current scientific beliefs limit the implantology choice to a tricompartmental prosthesis or two unicompartmental prostheses.

The need is therefore felt for a knee prosthesis which overcomes the drawbacks and prejudices of the prior art.

SUMMARY OF THE INVENTION

It is an object of the present invention to provide a knee prosthesis for the replacement of the medial and lateral femoral condyles, which allows saving bone tissue and better restoring the knee joint.

In particular, it is an object of the present is to preserve the healthy trochlea as much as possible.

It is another object of the present invention to provide a prosthesis which allows a better overall balance of the knee joint.

It is another object of the present invention to provide a prosthesis which can be easily implanted.

The present invention achieves at least one of such objects, and other objects which will become apparent in light of the present description, by means of a bicompartmental prosthesis, or bicondylar prosthesis, of the knee adapted to be fixed to a femur, the bicompartmental prosthesis comprising:
 a first portion adapted to define at least part of a medial femoral condyle;
 a second portion adapted to define at least part of a lateral femoral condyle;
 an interconnecting portion which integrally connects the first portion and the second portion to each other;
 the bicompartmental prosthesis being shaped so as to be adapted to leave the native trochlea at least partially uncovered; wherein along a same axis, a length of the first portion, in particular a maximum length of the first portion, is greater than a length of the second portion, in particular of a maximum length of the second portion.

In other words, said length of the second (i.e. lateral) portion is less than said length of the first (i.e. medial) portion.

In particular, the anterior end part of the second portion is lower than the anterior end part of the first portion. In other words, the anterior end part of the first portion protrudes with respect to the anterior end part of the second portion.

The prosthesis of the invention is particularly adapted to replace only two of the three knee compartments, namely the medial and lateral compartments, and more in particular only the medial femoral condyle and only the lateral femoral condyle.

The prosthesis of the invention is drastically different from a tricompartmental prosthesis, at least in that the tricompartmental prosthesis further comprises a portion adapted to replace the trochlea, while the prosthesis of the invention does not comprise the portion adapted to replace the trochlea, and preferably does not comprise portions adapted to replace the patella, although it may cooperate with a unicompartmental patella prosthesis, also referred to as a patellofemoral prosthesis.

Preferably, the prosthesis according to the invention is designed not to be connected to other prostheses for trochlea replacement; in particular, it is not provided with grafting zones for means of connection with a trochlea prosthesis.

The prosthesis is also drastically different from a "bi-mono" prosthetic implant, i.e., consisting of two unicompartmental prostheses because these are, completely, separate and implanted independently of each other.

The aforesaid first and second portions of the prosthesis of the invention are also named medial portion or medial condylar portion, and lateral portion or lateral condylar portion, respectively.

The medial portion, the lateral portion, and the interconnecting portion form a single femoral condylar carter.

Advantageously, with a single prosthesis (i.e. with a single component), it can be replaced the distal and posterior osseocartilaginous resections of the medial femoral condyle, by means of said medial portion of the prosthesis, and of the lateral femoral condyle, by means of said lateral portion of the prosthesis.

The prosthesis is indeed monolithic, i.e., it forms a single component. In particular, the medial condylar portion, the lateral condylar portion, and the interconnecting portion which joins them are mutually united and integrated.

The prosthesis advantageously avoids the resection of the native trochlea; in particular of the healthy native trochlea; or, at most, optionally, only its more distal or inferior portion of the intertrochlear groove can be resected.

In particular, advantageously, the prosthesis avoids the resection of the inferior-lateral portion of the trochlea (or inferior lateral trochlear portion), as will be explained in greater detail below.

The interconnecting portion (or connection portion) is also referred to as the intercondylar section or portion. In particular, the interconnecting portion can be, for example, an anterior or posterior intercondylar portion.

Advantageously, the interconnecting portion acts as a reinforcement, e.g., made of metal, adapted to absorb all stresses, in particular the shearing forces, the asymmetric compression forces of the condyles, and the forces produced by the asynchronous rolling and sliding movement, which could occur during all phases of gait, walking, and running.

Advantageously, the interconnecting portion does not conflict with the patellofemoral joint. In particular, preferably, the interconnecting portion does not conflict at all with the joint between patella and femur, or interferes only at the limit consisting of the trochlear condylar sulcus, in particular below it, to form, after the resection of the condyles, a continuum between trochlear cartilage and femoral condylar carter (i.e. the prosthesis).

Advantageously, the medial portion and the lateral portion are preferably asymmetric.

Advantageously, along a same axis (i.e. parallel to the same axis), a length of the first portion, in particular a maximum length of the first portion, is greater than a length of the second portion, in particular of a maximum length of the second portion.

In other words, advantageously, the medial portion is longer than the lateral portion.

In particular, the aforesaid difference in length between the medial portion and the lateral portion of the prosthesis of the invention is advantageous because it allows preserving also the lateral inferior trochlear portion.

Anatomically, the lateral trochlear portion, in its distal or inferior expansion, or downwards and posteriorly, in the anterior posterior direction, is wider than the medial one. Therefore, with a prosthesis according to the invention, it is avoided to intervening on all or substantially all the healthy lateral trochlea, which is therefore laterally preserved in both anterior and inferior positions.

Advantageously, the joint between patella and femur can be restored in the best manner after the implant of a prosthesis according to the invention.

More particularly, the articulation between femur and patella is respected, because only the part of the lateral condyle is replaced without altering its lateral trochlear portion.

Therefore, an advantageous technical effect of the prosthesis of the invention is to allow the effective, in particular complete, replacement of both condyles and, at the same time, to minimize, in particular, avoid, the resection of the lateral inferior trochlear portion, and more generally of the native trochlea.

Preferably, the difference in length, or height, between the medial portion and the lateral portion is from 2 to 4 mm, preferably from 2.5 to 3 mm.

The prosthesis of the invention is particularly but not exclusively suitable in cases of primitive (idiopathic) gonarthrosis, in particular when the patellar femoral compartment is not subject to the pathology in progress.

Advantageously, the prosthesis of the invention is corrective, in all senses, of any pathological alteration induced by osseocartilaginous wear, with no need of other cardan constraint implementation; it is not a resurfacing-only prosthesis; and/or it is not palliative of wear correction, as in the case of LCS prostheses, which have a rotating plate.

The prosthesis of the invention provides, in particular, the elimination of the incongruous and/or hybrid coupling between the metal trochlear shield (present in the femoral carter of tricompartmental prostheses) and patellar cartilage; or the elimination of the need for a polyethylene patellar prosthetic button against a metal femoral shield (currently mandatory in the USA), resulting in the canceling out either entirely or drastically 30% on average of patellar complications reported in the world literature as present in all total knee prostheses (TKP).

Preferably, in all embodiments, the first portion and the second portion mutually converge, particularly towards the anterior portion or area of the prosthesis, preferably at an angle from 15° to 33°, e.g., from 27° to 33°. More particularly, the longitudinal axis of the first portion and the longitudinal axis of the second portion mutually converge, preferably at an angle from 15° to 33°, e.g., from 27° to 33°.

It is particularly advantageous that the first portion and the second portion mutually converge because the anatomy of the knee is better respected.

The features of the prosthesis of the invention—in particular, the connection between the medial and lateral condylar portions, the shape adapted to leave the native trochlea at least partially uncovered, the difference in length between the medial and lateral portions and their preferable convergence—synergistically also lead to further advantages in addition to the preservation of the native trochlea, in particular the native inferior lateral trochlear portion.

In particular, as mentioned, the prosthesis of the invention does not involve the replacement of the patellofemoral joint. In other words, the prosthesis of the invention respects at most the patellofemoral joint and does not alter at all the asymmetric distal native construction of the medial condyle with respect to the higher one of the lateral condyle. Such a construction can be quantified in two manners: angular and by millimetric difference. The angular value is obtained by tangentially measuring the trochlear region forwards and the condyles, properly referred to, posteriorly, as medial and lateral, respectively, intended as the distal end of the femur as a whole. Under the same conditions, the millimetric difference in height is calculated between two tangents parallel to the trochlear apexes in relation to the straight line tangent of the posterior condyles. Advantageously, by analogy of calculation, the asymmetry of millimetric height or angular size, in the anterior-posterior direction, of the prosthesis of the invention "virtually" creates, when compared to the rectangular resection shape, described by John Insall—and either present or adopted or included by all the tricompartmental prosthetic models currently in use—a rather trapezoidal resective shape. This geometric figure comes out from a by necessity, but desired, asymmetric resection of the condyles as a whole. It is calculated for this purpose to achieve an optimal native balance, asymmetric per se, between the medial and lateral trochlea. In other words, the constructive asymmetry of the two prosthetic condyles is necessary to restore and/or respect the native centimetric asymmetry of the distal end of the femur when measured, on the horizontal plane, in relation to the apex of the medial trochlea, which will be lower or reduced, compared to the lateral one, higher or larger, for a previously mentioned difference, in particular, of 2-4 mm or 2.5-3 mm.

The native asymmetry of the distal end of the femur, as a whole, is respected if the medial condyle is resected in a higher or wider manner and the lateral one resected in lower or less extended manner, or, otherwise said, it is adopted a prosthesis like that of the invention, which, by design, has a higher or wider medial condyle, than the lateral one, lower or less extended, on the anteroposterior plane. All this, advantageously, does restore or faithfully reproduce the native form or restructures the whole distal end of the femur in native form, ex novo.

The prosthesis of the invention fully respects the anatomy and the function of the femoral quadriceps; it does respect and/or bring back to the absolute gaussian normality the relationship between the medial and lateral condyle; it fully respects the normal alignment of the lower limbs; it respects and/or restores the normal gaussian global axis of the lower limbs, in the three dimensions of the space, without creating any frontal or sagittal pathological laxity, with restoration of the total physiological flexion of the knee without further constructive artifacts inherent in the prosthesis itself, as in the so-called high flex prostheses.

Furthermore, particularly by virtue of its relative mini-invasiveness and the no need for proximal patellar and femoral soft tissue releases, the prosthesis of the invention allows reducing post-operative pain, blood loss, and therefore it can allow a better quality of life in relation to any pathological form of knee osteoarthritis, mainly of so-called "idiopathic" or primitive origin (the vast majority of forms present today) but also secondary forms of polytrauma, infections and serious morphological alterations of genetic, congenital and/or multifactorial origin.

The size of the prosthesis can be customized, e.g., in computerized mode and/or the prosthesis can be implanted with the help of a robot.

The prosthesis of the invention is easier to implant, both compared to a tricompartmental or to two unicompartmental or monocompartmental or to the so called bi-mono prostheses.

The implant can be performed advantageously with no intentional and dangerous medial release.

The prosthesis of the invention can be fixed to the femur by any fixing system. For example, of cemented type, even with non-smooth surfaces; non-cemented; hybrid, in particular with mixed anchorage systems, e.g. non-cemented tapers and "cement wire" cemented surfaces; optionally cross-linked poly with added vitamin E and/or titanium or steel reinforcements (or reinforcing elements); cross-linked or powdered titanium (T-pore); tantalum powder with or without additional screws and/or grooves and/or slots and/or various expansions; "all-poly" tapers and/or hydroxyapatite (HA) coated and/or resorbable and non-resorbable screws also coated with hydroxyapatite (HA).

The prosthesis of the invention is basically of CR (cruciate retaining) type, i.e., it allows the preservation of the posterior cruciate ligament (PCL) but its implantation is possible with sacrifice and/or replacement and/or substitution of PCL, substantially in any manner, and therefore it can be of PS (posterior stabilized) type.

The prosthesis of the invention is advantageously able to bring the knee back to normal, in particular, biomechanically speaking.

The prosthesis of the invention also allows reducing the length of the fixing pegs and reducing the number and size of the instruments for the implantation, and allows, in general, an overall reduction in term of costs and implant time.

Furthermore, the prosthesis, drastically, does allow reducing and/or eliminating the causes of cartilage wear, and therefore having, subsequently, a very positive effect—reduction and/or elimination—on the causes of wear of the prosthetic polyethylene; improving the tribological features; achieving a secure earlier popularization of knee prostheses (particularly at about forty years of age as onset disease); facilitating any subsequent re-prostheses; improving implant technology at once either under guidance and allows specialist-free implants with online computerized or software-guided remote assistance by means of an application; speeding up the implantation operation and reducing complications, both during and after the operation.

In this description, the terms "anterior" and "posterior" are used with reference to the implanted prosthesis when the knee is in extension. In orthostasis, an "anterior" part is inferior; and a "posterior" part remains posterior.

Further features and advantages of the present invention will become more apparent in light of the detailed description of preferred, but not exclusive embodiments.

The dependent claims describe particular embodiments of the invention.

BRIEF DESCRIPTION OF THE DRAWINGS

The description of the invention refers to the accompanying drawings, which are provided by way of non-limiting example, in which.

The same elements or parts have the same reference numerals.

DESCRIPTION OF EXEMPLARY EMBODIMENTS OF THE INVENTION

Examples of bicompartmental prosthesis 100, 100', or more particularly a bicondylar prosthesis 100, 100', according to the invention, are described with reference to the Figures.

Figure 7:
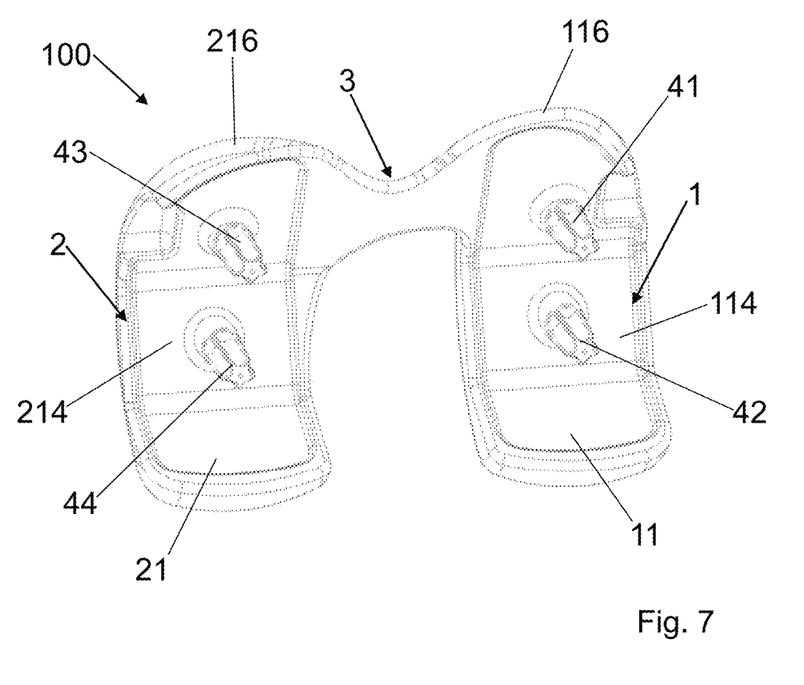
FIG. 7 shows another posterior perspective view of the prosthesis in FIG. 1.
Figure 8:
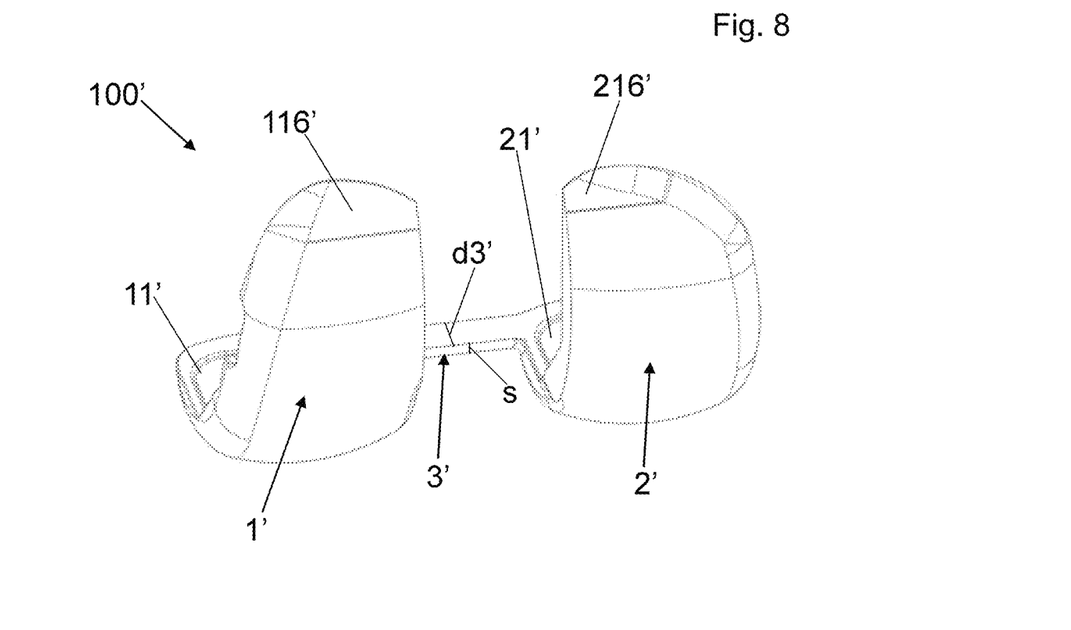
FIG. 8 shows a perspective view of the anterior side of another example of a left knee prosthesis according to the invention.
Figure 9:
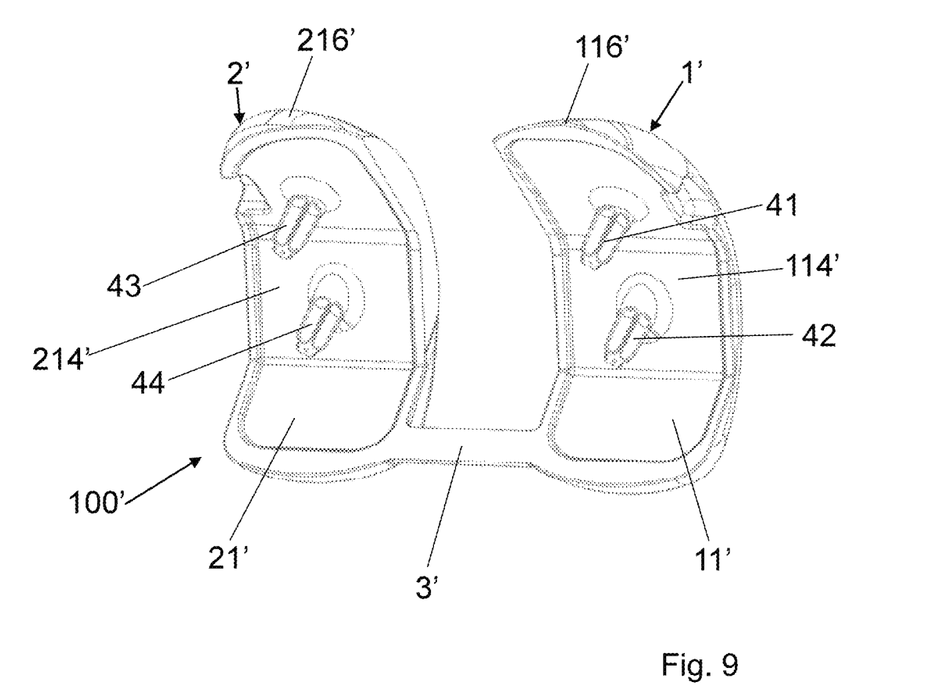
FIG. 9 shows a perspective view of another side, in particular of the posterior side, of the prosthesis in FIG. 8.

In particular, Figures from 1 to 7 show a first example of a left knee prosthesis 100 and FIGS. 8 and 9 show a second example of a left knee prosthesis 100'.

Although left knee prostheses are shown, the invention also relates to right knee prostheses. Those skilled in the art will be able to construct right knee prostheses according to the invention in light of this description.

The prosthesis 100, 100' of the invention is, in particular, a prosthesis configured to be implanted in a human being.

The prosthesis 100, 100' is, in particular, a femoral knee prosthesis, also referred to as a femoral component or femoral carter.

In all embodiments, the bicompartmental knee prosthesis 100, 100' is adapted to be fixed to a femur and comprises:

a first portion 1, 1' adapted to define a medial or internal femoral condyle, in particular, adapted to define a medial or internal femoral condyle, completely or partially (i.e., at least partially);

a second portion 2, 2' adapted to define a lateral or external femoral condyle, in particular, adapted to define a lateral or external femoral condyle, completely or partially (i.e., at least partially);

an interconnecting portion 3, 3' which integrally connects the first portion 1, 1' and the second portion 2, 2' to each other;

the bicompartmental prosthesis 100, 100' being shaped so as to be adapted to leave the native trochlea uncovered, at least partially, when the prosthesis 100, 100' is implanted.

The prosthesis 100, 100' is defined as bicompartmental because it is adapted to replace, in particular to replace only, the femoral part, in particular the inferior and posterior, of two of the three knee compartments, namely the medial femoral compartment and the lateral femoral compartment.

Preferably, the prosthesis 100, 100' is shaped, or configured, to be adapted to leave at least 90% of the native trochlea uncovered, e.g., 90% to 100%. In other words, once the prosthesis 100, 100' has been implanted, all or most of the trochlear surface is not covered by the prosthesis 100, 100' and only a smaller portion of the trochlea can optionally be covered by the prosthesis 100, 100'. In particular, only the more distal or inferior portion of the trochlea, more particularly the portion extending up to 3 or 4 mm around the anterior inferior intertrochlear groove, may optionally be covered by the prosthesis 100, 100', in particular by the prosthesis 100.

The prosthesis 100 shown in FIGS. 1 to 7, in particular, is shaped to leave at least 90% of the trochlea (or trochlear surface) uncovered, e.g., about 90%. In other words, the prosthesis 100 covers at most 10% of the trochlea, e.g., it covers 10% of the trochlea. However, in variants not illustrated, the prosthesis 100 is shaped to leave the native trochlea completely (i.e. 100%) uncovered.

The prosthesis 100' shown in FIGS. 8 and 9 is, in particular, shaped so as to be adapted to leave the native trochlea completely (i.e. 100%) uncovered. However, in variants not shown, the prosthesis 100' is shaped to leave less than 100% of the trochlea uncovered, and preferably at least 90% of the trochlea.

The prosthesis 100, 100' comprises an outer surface and an inner surface, opposite to each other. The inner surface is, in particular, destined to face the femur.

Preferably, the first portion 1, 1' and the second portion 2, 2' each have a thickness from 6 to 8 mm. Such a thickness is, in particular, the distance between the inner surface of the first portion 1, 1' and the outer surface of the first portion 1, 1', and similarly for the second portion 2, 2'.

The outer surface of the first portion 1, 1' is adapted to define at least part of a medial femoral condyle, and the outer surface of the second portion 2, 2' is adapted to define at least part of a lateral femoral condyle.

Therefore, the outer surface of the first portion 1, 1' and the outer surface of the second portion 2, 2' are at least partially convex, in particular predominantly or completely convex, more particularly on the two frontal and sagittal planes.

The first portion 1, 1' is in particular adapted to cover, at least partially, the resection of a medial femoral condyle, and the second portion 2, 2' is particularly adapted to cover, at least partially, the resection of a lateral femoral condyle.

The first portion 1, 1' and the second portion 2, 2' comprise a respective end part 11, 21, 11', 21', also referred to as posterior parts or posterior end parts. The two end parts 11, 21, 11', 21' are destined to be posterior parts of the prosthesis 100, 100' when it is implanted, being particularly posterior when the knee is in extension.

The first portion 1, 1' and the second portion 2, 2' further comprise a respective anterior part 116, 216, 116', 216', or anterior end part. The two end parts 116, 216, 116', 216' are destined to be anterior parts of the prosthesis 100, 100' when it is implanted, being in particular anterior when the knee is in extension. In general, when the prosthesis 100, 100' is implanted, the two end parts 116, 216, 116', 216' are destined to be proximal with respect to the trochlea and the two end parts 11, 21, 11', 21' are destined to be distal with respect to the trochlea. Therefore, the end parts 116, 216, 116', 216' may also be named "proximal parts" with respect to the trochlea and the end parts 11, 21, 11', 21' may also be named "distal parts" with respect to the trochlea.

Figure 6:
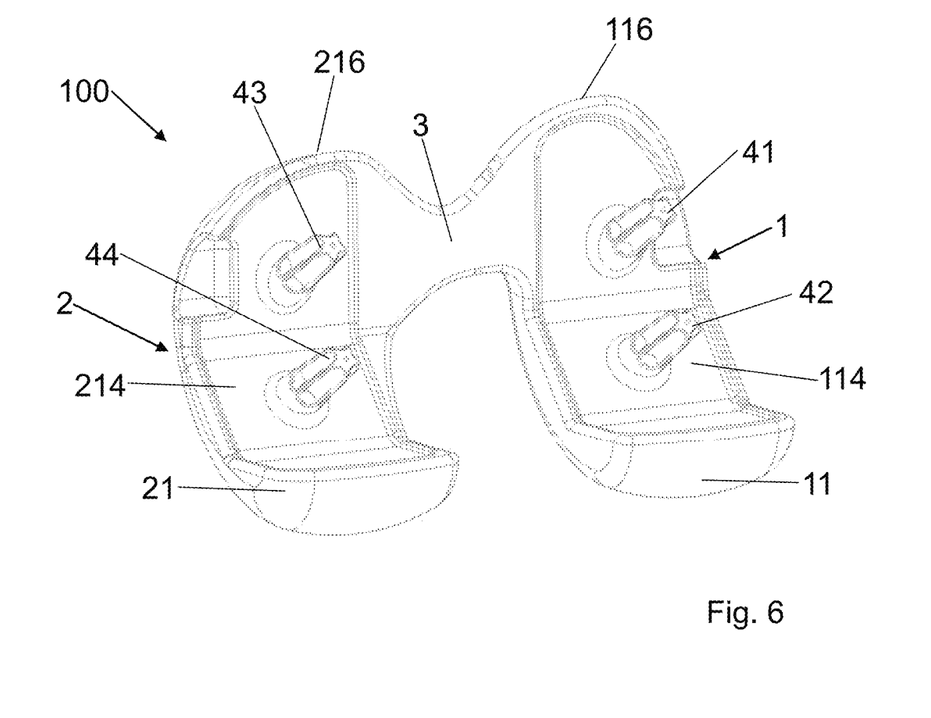
FIG. 6 shows another posterior perspective view of the prosthesis in FIG. 1.

The part of the first portion 1, 1' extending between the posterior end part 11, 11' and the anterior end part 116, 116' is indicated with reference numeral 114, 114' (FIGS. 6, 7, and 9).

The part of the second portion 2, 2' which extends between the posterior end part 21, 21' and the anterior end part 216, 216' is indicated by reference numeral 214, 214' (FIGS. 6, 7, and 9).

The parts 114, 114', 214, 214' are also named chanfreins (in French).

Figure 1:
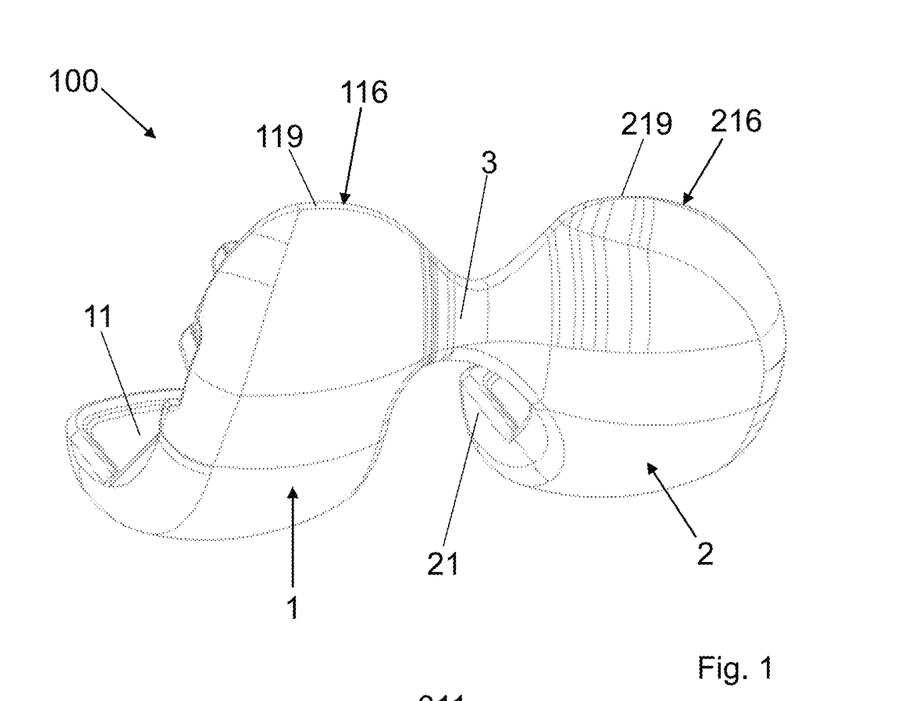
FIG. 1 shows a perspective view of an example of a left knee prosthesis according to the invention.
Figure 2:
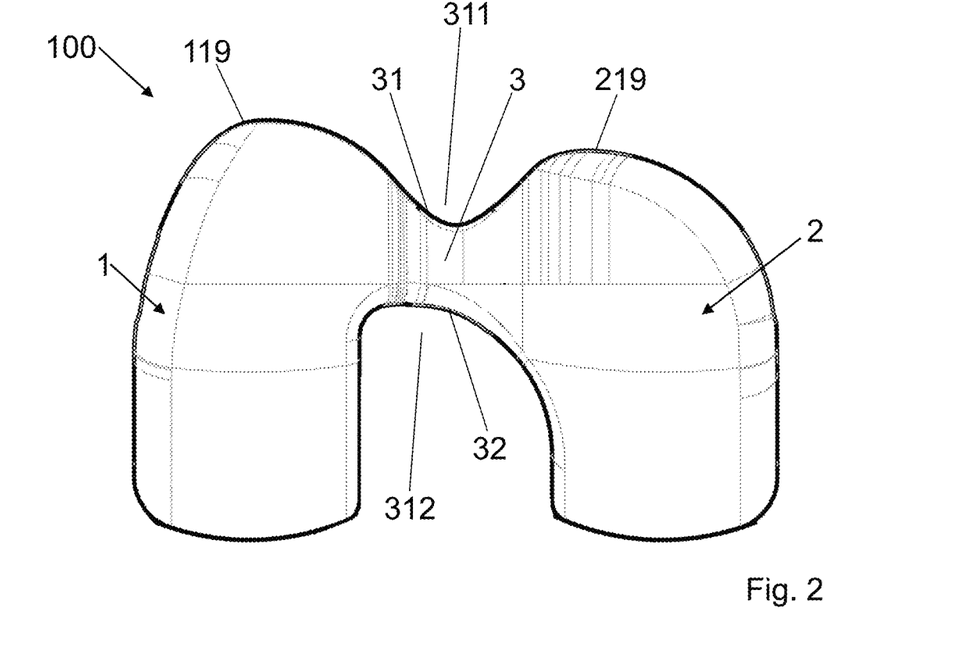
FIG. 2 shows a front view of the anterior side of the prosthesis in FIG. 1.
Figure 3:
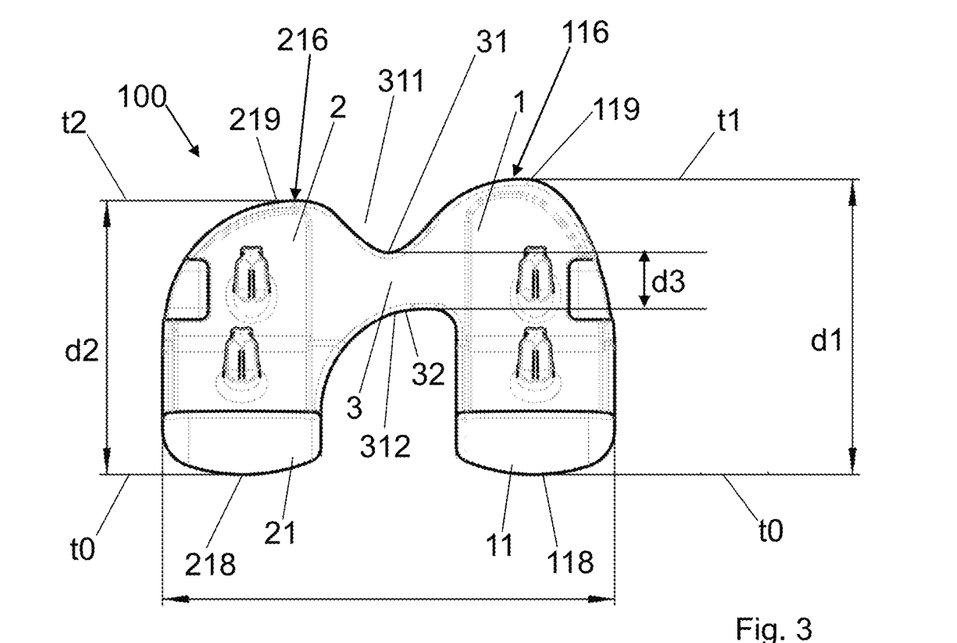
FIG. 3 shows a view of the posterior side of the prosthesis in FIG. 1.
Figure 4:
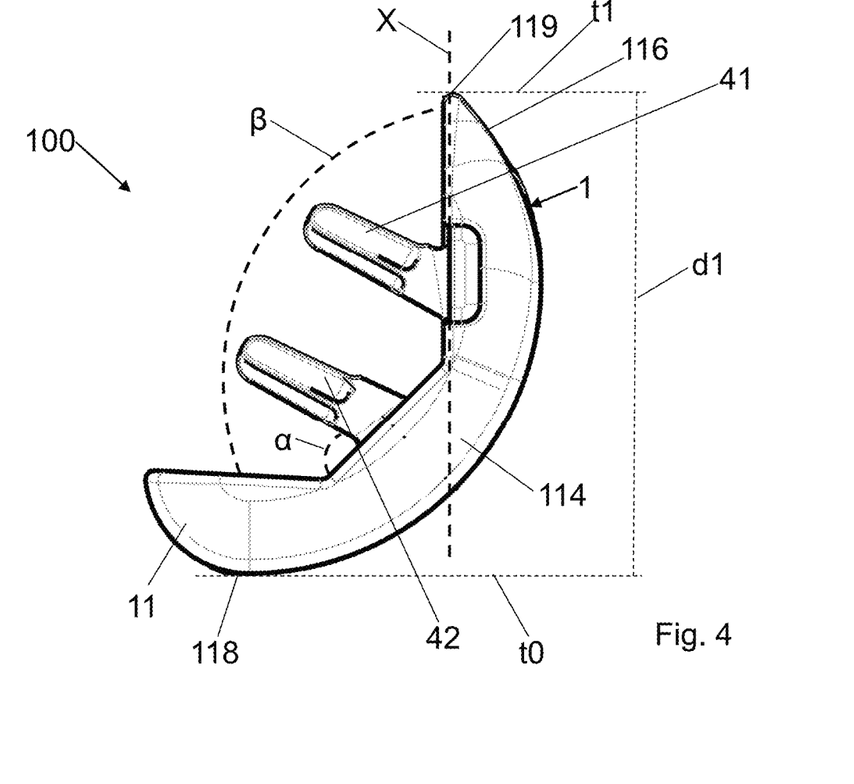
FIG. 4 shows a side view of the prosthesis in FIG. 1.
Figure 5:
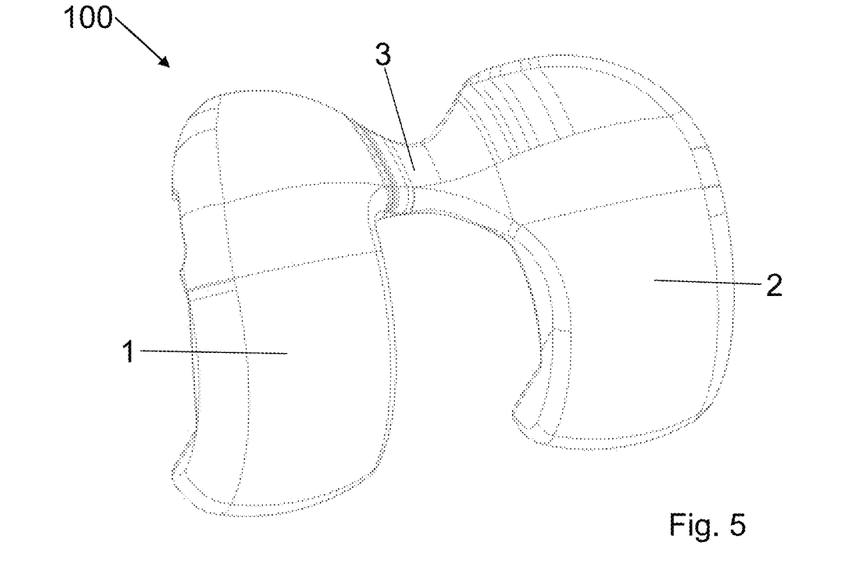
FIG. 5 shows another front perspective view of the prosthesis in FIG. 1.

Along an axis X, the first portion 1, 1' has a length, in particular a maximum length, indicated by the reference symbol d1 (FIGS. 3 and 4). Along the same X axis, the second portion 2, 2' has a length, in particular a maximum length, indicated by reference symbol d2.

The length d1 is advantageously greater than the length d2. Preferably, the difference in length between the length d1 and the length d2 is from 2 to 4 mm, preferably from 2.5 to 3 mm. In other words, the first portion 1, 1', i.e. the medial portion, has a length d1, or height, greater than the length d2 of the second portion 2, 2', i.e. the lateral portion.

Advantageously, as explained above, such a difference in length allows the preservation of the inferior lateral part of the trochlea (i.e. the native lateral inferior trochlear portion) and allows the best possible restoration of the patellofemoral joint after implanting a prosthesis according to the invention.

In particular, the anterior end part 216, 216' of the second portion 2, 2' is lower than the anterior end part 116, 116' of the first portion 1, 1'. In other words, the anterior end part 116, 116' of the first portion 1, 1' protrudes with respect to the anterior end part 216, 216' of the second portion 2, 2'.

Preferably, the length d1 is from 3.5 to 6 cm (i.e. from 35 to 60 mm) and/or the length d2 is from 3.1 to 5.8 cm (i.e. from 31 to 58 mm).

The axis X along which the two lengths d1, d2 are measured is, in particular, an axis perpendicular to the tangent t0 to the outer surface of the end parts 11, 21, 11', 21' and to the tangent t1, t2 to the anterior end part 119, 219 of the first portion 1, 1' and of the second portion 2, 2', respectively. In particular, the aforementioned axis X is straight. Said tangents t1 and t2 are distinct from each other. Said tangents t0, t1, t2, or tangent lines, are preferably parallel to one another.

More particularly, for the first portion 1, 1', the tangent t0 at the posterior end 118 of the end portion 11, 11' and the tangent t1 at the anterior end 119 of the first portion 1, 1' are considered.

Similarly, for the second portion 2, 2', the tangent t0 at the posterior end 218 of the end portion 21, 21' and the tangent t2 at the anterior end 219 of the second portion 2, 2' are considered.

Preferably, but not exclusively, the tangent t0 is tangent to both the posterior end part 11, 11' and the posterior end part 21, 21'. In this case, the posterior end part 11, 11' and the posterior end part 21, 21' are substantially at the same level.

Preferably, the anterior end 119 and the anterior end 219 are convex or at least partially convex, particularly towards the outside.

The anterior end 119 and the anterior end 219 define an end edge of the first portion 1, 1' and the second portion 2, 2', respectively, and this edge is convex or at least partially convex.

In more general terms, preferably the axis X along which the two lengths d1, d2 are measured extends from a posterior to an anterior area of the prosthesis, in particular when the knee is in extension. In particular, the posterior area of the prosthesis 100, 100' comprises the posterior end parts 11, 21, 11', 21'; and the anterior area comprises the anterior end parts 116, 216, 116', 216'.

Preferably, the first portion 1, 1' and the second portion 2, 2' mutually converge, particularly towards the anterior portion or area of the prosthesis 100, 100', preferably at an angle of 15° to 33°, e.g., from 27° to 33°. More particularly, the longitudinal axis of the first portion 1, 1' and the longitudinal axis of the second portion 2, 2' converge, preferably with an angle from 15° to 33°, e.g., from 27° to 33°.

It is particularly advantageous that the first portion 1, 1' and the second portion 2, 2' converge, as the anatomy of the knee is best respected.

The first portion 1, 1', the second portion 2, 2' and the interconnecting portion 3, 3' form a single monolithic component.

Preferably, the prosthesis 100, 100' is made of metal and/or polymer material. For example, the prosthesis 100, 100' can be made of steel or titanium. Preferably, the prosthesis 100, 100' is made of Cr—Co—Mo alloy, optionally Nickel-free. The prosthesis 100, 100' can also be made, for example, of polymer material, e.g., such as polyethylene, with a metal inner core, e.g., made of steel or titanium.

The interconnecting portion 3, 3' extends, in particular, transversally, to the first portion 1, 1' and the second portion 2, 2'.

Preferably, there is provided only one interconnecting portion 3, 3' which integrally connects the first portion 1, 1' and the second portion 2, 2' to each other.

The remaining part of the gap between the first portion 1, 1' and the second portion 2, 2' is preferably empty.

The interconnecting portion 3, 3' has a thickness (shown for example in FIG. 8 by reference symbol "s") preferably from 3 to 8 mm, e.g., from 5 to 8 mm or from 3 to 5 mm or from 3 to 6 mm.

In particular, the thickness of the interconnecting portion 3 is preferably from 5 to 8 mm and the thickness "s" of the interconnecting portion 3' is preferably from 3 to 5 mm or from 3 to 6 mm.

The thickness is measured along a transverse axis, in particular orthogonal, to the inner surface and/or the outer surface of the interconnecting portion 3, 3'. In other words, the thickness of the interconnecting portion 3, 3', substantially, corresponds to the distance between the inner surface and the outer surface of the interconnecting portion 3, 3'.

Optionally, the inner surface of the interconnecting portion 3, 3' is convex, preferably having a thickening which provides greater structural strength. For example, the inner surface of the interconnecting portion 3 may comprise a spherical cap-shaped, e.g., hemispherical, part.

The interconnecting portion 3' can be shaped, for example, like a parallelepiped, and in this case, preferably the thickness "s" is from 3 to 5 mm, or it can be shaped like a cylinder, and in this case, preferably the thickness "s" is from 3 to 6 mm and corresponds to the diameter of the cylinder.

The interconnecting portion 3, 3' has a height d3, d3' (FIGS. 3 and 8), in particular, perpendicularly to the thickness, preferably, from 4 to 16 mm, e.g., from 8 to 16 mm or from 4 to 8 mm.

In particular, the interconnecting portion 3 has preferably a height d3 from 8 to 16 mm, and the interconnecting portion 3' has preferably a height d3' from 4 to 8 mm (e.g., when it is parallelepiped shaped) or from 3 to 6 mm (e.g., when it is cylinder-shaped).

In the example shown in Figures from 1 to 7, the interconnecting portion 3 is distal from the end parts 11, 21. In particular, preferably, the interconnecting portion 3 extends between the two anterior end parts 116, 216, preferably joining them. Preferably, in this example, the height d3 (FIG. 3) is measured along the same axis X along which lengths d1 and d2 are measured.

Preferably, in this example, the interconnecting portion 3 is destined to occupy, the high cartilage connection space of the intertrochlear groove. In particular, the interconnecting portion 3 is preferably adapted not to conflict with the patellofemoral joint or, at most, just at the limit consisting of the condylar-trochlear osseocartilaginous sulcus, or below it, in particular to preserve, after resection, a continuum between trochlear cartilage and the prosthesis 100.

Preferably, between the first portion 1 and the second portion 2 there are two inlets 311, 312, or grooves, opposite to each other.

The inlet 311 is particularly shaped to follow the curvilinear course of the intertrochlear groove, in particular of its anterior and inferior part of the trochlea.

The inlet 312 is particularly shaped so as not to conflict with the posterior cruciate ligament (PCL) in the insertion proximal to the femur (anteromedial).

The inlet 311 is delimited, at least partially, by a surface portion 31 of the interconnecting portion 3, and the inlet 312 is delimited, at least partially, by another surface portion 32 of the interconnecting portion 3. The surface portion 31 and the surface portion 32 are opposite to each other. The surface portion 31 is substantially concave and/or the surface portion 32 is substantially concave. Preferably, the surface portions 31, 32 have opposite concavities and are, preferably, asymmetric.

In this example, the aforesaid height d3 corresponds to the distance between the surface portion 31 and the surface portion 32 of the interconnection portion 3, and is preferably from 8 to 16 mm.

In the example shown in FIGS. 8 and 9, the interconnecting portion 3' is proximal to the end parts 11', 21'. In particular, preferably, the interconnecting portion 3' extends between the end parts 11', 21', and, in particular, joins them.

In all embodiments, preferably, the prosthesis 100, 100' comprises at least two fixing pegs 41, 42, 43, 44 to fix the prosthesis 100, 100' to the femur. In particular, the first portion 1, 1' and the second portion 2, 2' each comprise at least one fixing peg 41, 42, 43, 44.

Preferably, the first portion 1, 1' is provided with two fixing pegs 41, 42 and the second portion 2, 2' is provided with two fixing pegs 43, 44.

With reference to the first portion 1, 1', the peg 42 is proximal to the end portion 11, 11' and the peg 41 is distal from the end portion 11, 11'. Preferably, the peg 42 extends from the inner surface of part 114, 114' (FIGS. 4, 6, 7 and 9), and preferably the peg 41 extends from the inner surface of the anterior end part 116, 116'.

With reference to the second portion 2, 2', the peg 44 is proximal to the end portion 21, 21' and the peg 43 is distal from the end portion 21, 21'.

Preferably, the peg 44 extends from the inner surface of part 214, 214', and preferably the peg 43 extends from the inner surface of the anterior end part 216, 216'.

The peg 41 and the peg 42 are preferably parallel to each other; and the peg 43 and the peg 44 are preferably parallel or substantially parallel to each other. Preferably, the pegs 41, 42, 43, and 44 are parallel to one another.

Each peg 41, 42, 43, 44 extends transversely from the inner surface of the prosthesis 100, 100'. In particular, preferably, the pin 42 forms an acute angle α (FIG. 4), e.g., from 25° to 30°, with the surface from which it extends, said acute angle being proximal to the end portion 11, 11'. Similarly, the peg 44 forms an acute angle, e.g., from 25° to 30° with the surface from which it extends, said acute angle being proximal to the end portion 21, 21'. Preferably, each peg 41, 42, 43, 44 has a length from 8 to 12 mm, e.g., equal to or about 10 mm. The length of a peg 41, 42, 43, 44 is measured from its base at the inner surface of the prosthesis 100, 100', at its distal end from the inner surface of the prosthesis 100, 100'.

The thickness, or diameter, of each peg 41, 42, 43, 44 is preferably from 4 to 8 mm, e.g., about or equal to 5 mm.

Pegs 41, 42, 43, 44 may have various shapes, e.g., cylindrical, morse taper, or with a plurality of flanges, e.g., three, four, five, or more flanges.

In all embodiments, preferably, no inner surface portion of the prosthesis 100, 100' faces the inner surface of said end parts 11, 21, 11', 21'. In particular, no portion of the inner surface of the first portion 1, 1' faces the inner surface of the end part 11, 11' and no portion of the inner surface of the second portion 2, 2' faces the inner surface of the end part 21, 21'. Only the pegs 41, 42, 43, 44, e.g., the pegs 42, 44, may optionally face the end portion 11, 11' and the end portion 21, 21', respectively.

Preferably, the inner surface of the posterior end portion 11, 11' forms an angle β with the inner surface of the anterior end portion 116, 116' (FIG. 4) greater than or equal to 87°, e.g., from 87° to 90° or from 87° to 89° or from 88° to 90° or 88° to 89°.

Said angle β is, in particular, an angle the vertex of which is proximal to the lateral surface and therefore distal from the inner surface of the prosthesis 100, 100'.

Similarly, the inner surface of the end portion 21, 21' also forms, with the inner surface of the anterior end portion 216, 216' an angle greater than or equal to 87°, e.g., from 87° to 90° or from 87° to 89° or from 88° to 90° or from 88° to 89°, preferably equal or substantially equal to said angle β.

The width of the aforesaid angle, inter alia, advantageously allows the presence of two fixing pegs 41, 42, 43, 44 for each portion 1, 1', 2, 2'. The presence of two fixing pegs 41, 42, 43, 44 for each portion 1, 1', 2, 2', advantageously allows obtaining the pegs 41, 42, 43, 44 with a limited length.

In all the embodiments, preferably, the radius of curvature of the outer surface of the first portion 1, 1' is substantially unique, both frontally and sagittally, and has preferably an average value from 2.2 to 2.6 cm, e.g., about 2.5 cm. The same applies for the second portion 2, 2'.

Optionally, only part of the outer surface of each end portion 11, 11', 21, 21' has a different, and in particular smaller, radius of curvature than the radius of curvature of the remaining part of the first portion 1, 1' and of the second portion 2, 2'.

Figure 10:
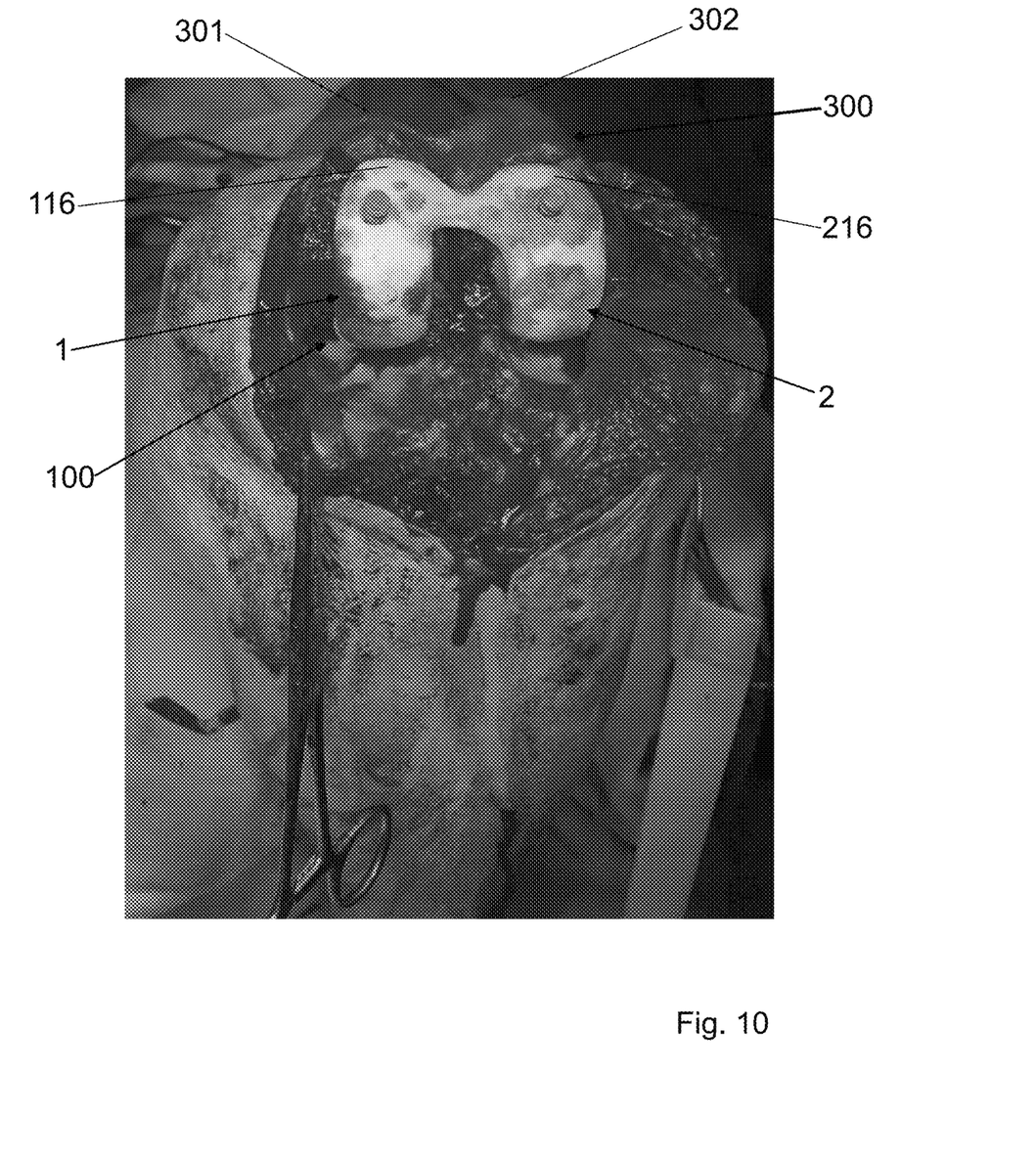
FIG. 10 shows a phantom of the prosthesis in FIG. 1 implanted.

An important advantage of a prosthesis 100 according to the invention can be appreciated in FIG. 10, where the phantom of an implanted left prosthesis is shown. A similar result can be achieved by means of a prosthesis 100'.

It is worth noting, in particular, that the anterior end part 216 of the second portion 2 is at a distal height or level than the anterior end part 116 of the first portion 1 (as explained above).

The trochlea is indicated by reference numeral 300.

The dome 301 of the trochlea 300 is at the first portion 1; and the dome 302 of the trochlea 300 is at the second portion 2.

Advantageously, the prosthesis 100 allows keeping the dome 302 at a higher height or level than the dome 301. This is particularly advantageous because the natural anatomy of the knee is actually respected.

All known prostheses, on the other hand, in particular tricompartmental prostheses, imply the undesirable and disadvantageous risk that—once the prosthesis has been implanted—the dome 301 will be at an equal or greater height than the dome 302 (a condition that causes at least 30% of the prosthesis revisions, as widely reported in the world scientific literature).

The invention claimed is:

1. A bicompartmental knee prosthesis, or bicondylar prosthesis, adapted to be fixed to a femur, the prosthesis comprising
   a medial portion adapted to define a medial femoral condyle;
   a lateral portion adapted to define a lateral femoral condyle;
   an interconnecting portion which integrally connects the medial portion and the lateral portion to each other;
   the prosthesis being shaped so as to be adapted to leave the native trochlea at least partially uncovered;
   wherein said medial portion and said lateral portion of the prosthesis comprise a respective posterior end part; said posterior end parts being posterior parts of the prosthesis, when the prosthesis is implanted and the knee is in extension;
   wherein said medial portion and said lateral portion of the prosthesis comprise a respective anterior end part, said anterior end parts being anterior parts of the prosthesis, when the prosthesis is implanted and the knee is in extension;
   wherein the posterior end part of the medial portion has a posterior end and the posterior end part of the lateral portion has a posterior end;
   wherein the anterior end part of the medial portion has an anterior terminal end, which is the anterior terminal end of said medial portion, and the anterior end part of the lateral portion has an anterior terminal end, which is the anterior terminal end of said lateral portion;
   wherein said anterior terminal end of the medial portion defines an end edge of the medial portion, and said anterior terminal end of the lateral portion defines an end edge of the lateral portion;
   wherein, along a same axis, the maximum length of the medial portion is greater than the maximum length of the lateral portion,
   said axis being an axis perpendicular to a tangent to an outer surface of each of said posterior end parts,
   and perpendicular to the tangents to the anterior terminal ends of the medial portion and of the lateral portion, respectively.

2. The prosthesis according to claim 1, shaped so as to be adapted to leave at least 90% of the native trochlea uncovered.

3. The prosthesis according to claim 1, shaped so as to be adapted to leave the native trochlea completely uncovered.

4. The prosthesis according to claim 1, wherein the medial portion and the lateral portion mutually converge towards an anterior portion or area of the prosthesis.

5. The prosthesis according to claim 1, wherein said medial portion, said lateral portion and said interconnecting portion form a single monolithic component.

6. The prosthesis according to claim 1, wherein said maximum length of the medial portion is from 2 to 4 mm or from 2.5 to 3 mm greater than said maximum length of the lateral portion.

7. The prosthesis according to claim 1, comprising only one interconnecting portion which integrally connects the medial portion and the lateral portion to each other.

8. The prosthesis according to claim 1, wherein each anterior end part forms an angle greater than or equal to 87° with the respective posterior end part.

9. The prosthesis according to claim 8, wherein said angle is from 87° to 90°.

10. The prosthesis according to claim 1, wherein said axis, along which said length of the medial portion and said maximum length of the lateral portion are measured, extends from a posterior area to an anterior area of the prosthesis when the knee is in extension.

11. The prosthesis according to claim 1, wherein said maximum length of the medial portion is from 3.5 to 6 cm and/or said maximum length of the lateral portion is from 3.1 to 5.8 cm.

12. The prosthesis according to claim 1, wherein a first inlet and a second inlet opposite to each other are provided between the medial portion and the lateral portion.

13. The prosthesis according to claim 1, wherein when the prosthesis is implanted said anterior terminal end of the lateral portion is closer to said tangent to the outer surface of each of said posterior end parts; and said anterior terminal end of the medial portion is farther from said tangent to the outer surface of each of said posterior end parts.

* * * * *